United States Patent
Kumar et al.

(10) Patent No.: US 9,758,460 B2
(45) Date of Patent: Sep. 12, 2017

(54) PROCESS FOR RECOVERY OF PURE COMPONENTS FROM PRODUCT MIXTURE OF ONE STEP DIMETHYL ETHER SYNTHESIS REACTOR

(71) Applicant: Council of Scientific & Industrial Research, New Delhi (IN)

(72) Inventors: Sunil Kumar, Dehradun (IN); Nanoti Shrikant Madhusudan, Dehradun (IN); Garg Madhukar Onkarnath, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/164,743

(22) Filed: May 25, 2016

(65) Prior Publication Data

US 2016/0347697 A1    Dec. 1, 2016

(30) Foreign Application Priority Data

May 26, 2015    (IN) .......................... 1492/DEL/2015

(51) Int. Cl.
| | |
|---|---|
| *C07C 41/42* | (2006.01) |
| *C07C 43/04* | (2006.01) |
| *C07C 41/34* | (2006.01) |
| *C07C 41/38* | (2006.01) |
| *C07C 41/40* | (2006.01) |

(52) U.S. Cl.
CPC .............. *C07C 41/42* (2013.01); *C07C 41/34* (2013.01); *C07C 41/38* (2013.01); *C07C 41/40* (2013.01)

(58) Field of Classification Search
CPC ........ C07C 41/01; C07C 43/043; C07C 41/34; C07C 41/38; C07C 41/42
See application file for complete search history.

(56) References Cited

U.S. PATENT DOCUMENTS

| | | |
|---|---|---|
| 5,908,963 A | 6/1999 | Voss et al. |
| 6,458,856 B1 | 10/2002 | Peng et al. |
| 7,652,176 B2 | 1/2010 | Madsen |
| 7,910,630 B2 | 3/2011 | Rostrup-Nielsen et al. |
| 8,835,517 B2 | 9/2014 | Cheiky et al. |
| 2010/0216897 A1 | 8/2010 | Rostrup-Nielsen |

FOREIGN PATENT DOCUMENTS

EP    2070905 A1    6/2009

*Primary Examiner* — Medhanit Bahta
(74) *Attorney, Agent, or Firm* — Knobbe, Martens, Olson & Bear, LLP (57) ABSTRACT

A process separates pure components from a product mixture produced by a one-step dimethyl ether synthesis reactor. The product mixture is scrubbed with pure dimethyl ether followed by scrubbing with aqueous methanol solvent in two absorption columns to reduce $CO_2$ level and to minimize methanol and dimethyl ether loss with the recovered unconverted synthetic gas. The pure water or aqueous methanol is mixed with the vapor stream of $CO_2$ separation distillation. Dimethyl ether, methanol and water mixture are separated. A scheme for separation of methanol and water mixture minimizes the size, energy and cost of separation. The process can be cost-effective, energy-efficient, environment-friendly and readily-miniaturized.

15 Claims, 3 Drawing Sheets

PROCESS FOR RECOVERY OF PURE COMPONENTS FROM PRODUCT MIXTURE OF ONE STEP DIMETHYL ETHER SYNTHESIS REACTOR

INCORPORATION BY REFERENCE TO ANY PRIORITY APPLICATIONS

This application is the U.S. Non-Provisional Application claiming priority to Indian Patent Application No. 1492/DEL/2015, filed May 26, 2015, which is hereby incorporated by reference.

In addition, any and all applications for which a foreign or domestic priority claim is identified in the Application Data Sheet as filed with the present application are hereby incorporated by reference under 37 CFR 1.57.

BACKGROUND OF THE INVENTION

Field of the Invention

Present invention relates to a process for recovery of pure components from product mixture of one step dimethyl ether synthesis reactor. More particularly, the present invention relates to a energy efficient and cost effective process for recovery of unconverted synthetic gas lean in $CO_2$, $CO_2$ stream with minimized content of diethyl ether to enhance the process diethyl ether productivity, recovery of dimethyl ether product, and methanol to be either recycled to dimethyl ether synthesis reactor or to be withdrawn as a product and water.

Description of the Related Art

In one step dimethyl ether (DME) production process, synthetic gas is catalytically converted in DME in a single rector with methanol synthesis ($2H_2+CO=CH_3OH$), methanol dehydration ($2CH_3OH=CH_3OCH_3+H_2O$) and water gas shift reaction ($CO+H_2O=CO_2$). The overall reaction for synthesis gas conversion to DME is: $3H_2+3CO=CH_3OCH_3+CO_2$. Formation of methanol and DME is limited by the chemical equilibrium. Per pass syngas conversion or productivity of one step DME synthesis reactor will depend on the synthetic gas composition, reactor pressure and temperature significantly due to chemical synergy among reactions involved. It is apparent to understand that higher per pass syngas conversion or productivity of DME synthesis reactor would lead to small size and lower operating cost of the reactor, separation and recycles systems. The product mixture from one step DME synthesis reactor will be a mixture of unconverted synthetic gas, DME, $CO_2$, methanol and water.

The separation systems for production of pure DME and DME rich stream from the product mixture of one step DME reactor have been disclosed in published literature [U.S. Pat. No. 5,908,963; Pat. No. U.S. Pat. No. 6,458,856 B1; Pat. No. US2010/0216897; Pat. No. U.S. Pat. No. 7,910,630 B2; Pat No. EP2070905A1; Pat. No U.S. Pat. No. 7,652,176 B2; Pat. No. U.S. Pat. No. 8,835,517 B2].

U.S. Pat. No. 5,908,963 discloses a process for preparation of fuel grade dimethyl ether (DME). In this patent unconverted synthetic gas is separated from other compounds using condensation and methanol absorption based separation system. The recovered synthetic gas is recycled to DME synthesis reactor. The major focus is given on production of fuel grade DME containing significant amount of methanol. The removal of $CO_2$ from synthesis gas is not mentioned in the patent.

U.S. Pat. No. 6,458,856 B1 discloses a process for one step production of dimethyl ether (DME) from synthetic gas. The DME reactor effluent is separated into vapor mixture comprising DME, $CO_2$ and unconverted synthetic gas and liquid stream comprises of DME, methanol and $CO_2$ using high pressure flash. The vapor mixture is scrubbed with the scrubbing solvent comprising methanol and DME mixture to remove the $CO_2$. The recovered synthetic gas lean in $CO_2$ lean is recycled to DME synthesis reactor. DME, methanol, $CO_2$, and water were recovered from the liquid mixture using number of flash and distillation column. Invention claims the novelty for improvement in reduction of $CO_2$ and DME concentration in recycled synthetic gas achieved by using DME and methanol mixture as scrubbing solvent in comparison to pure DME as scrubbing solvent.

Pat. No. US2010/0216897 discloses a process where pure DME and methanol were used as scrubbing solvents in two separate zones of the absorption column to recover the $CO_2$ lean synthetic gas. It was mentioned that invention utilizes the higher solubility of $CO_2$ in DME to minimize the quantity requirement of scrubbing solvent for reducing the $CO_2$ concentration to desired level and utilizes the lower vapor pressure of methanol to minimize the loss of scrubbing solvent (methanol+DME) in recovered synthetic gas to be recycled to DME synthesis reactor.

U.S. Pat. No. 7,910,630 B2 discloses a method in which methanol and water mixture from DME reactor effluent is removed using condensation. A cooled solvent of dialkyl ether of a polyethelene glycol was used to scrub the $CO_2$ and DME from uncondensed syngas. The scrubbed gas is recycled to DME reactor. The $CO_2$ and DME are selectively desorbed in the subsequent steps.

Pat. No. EP 2070905A1 discloses a process in which a product mixture from DME reactor is scrubbed with a liquid solvent being rich in dialkyl ether of a polyalkylene glycol. The dissolved $CO_2$ and DME in solvent are separated using the distillation columns. Condensed methanol water mixture is either recycled to DME synthesis reactor or passing to methanol dehydration reactor. No separation of condensed methanol water mixture is disclosed. The one of ordinary skilled in the art can understand that for stable operation water draw off from process is required to maintain the water concentration in the process.

U.S. Pat. No. 7,652,176 B2 assigned to Haldor Topsoe discloses a process in which product mixture obtained from the DME reactor is scrubbed with a liquid solvent being rich in potassium carbonate or amine for selective absorption of carbon dioxide in liquid solvent to reduce the $CO_2$ in the recycled unconverted synthetic gas. An additional solid adsorbent comprised of Zeolite, molecular sieves or activated alumina is used to further reduce the $CO_2$ concentration in the recycled unconverted synthetic gas. Subsequently, distillations columns were used to separate the solvent, DME, $CO_2$ and methanol from the mixture thereof.

U.S. Pat. No. 8,835,517 B2 discloses a method that uses chilled water for scrubbing the DME and methanol from DME reactor product mixture in high pressure absorption column. Mixture of water, DME, $CO_2$ is preheated in a heat exchanger and flashed in lower pressure column. A DME rich stream is generated from this flash column. The unconverted syngas produced is lean in DME and $CO_2$. However, the concentration of dimethyl ether in DME rich stream and concentration of DME and $CO_2$ in recovered unconverted synthetic gas are not disclosed. Moreover, $CO_2$ removal from DME and water is also not addresses.

It is important to note that methods disclosed in the prior art for DME production using one step DME synthesis rector are focused on; reducing the concentration of $CO_2$ in unconverted synthetic gas using solvents like DME, methanol, chilled water, mixture thereof, dialkyl ether, potassium carbonate or amine rich solvents; minimizing the concentration of scrubbing solvent in unconverted synthetic gas to be recycled to the DME synthesis reactor. Pat. No. US2010/0216897 describes that how application of pure DME and methanol in two separate zone of absorption column is more effective in terms of requirement of less quantity of scrubbing solvent, lower concentration of $CO_2$ in recovered unconverted synthetic gas and less loss of DME and methanol with the recovered unconverted synthetic gas in comparison to using the mixture of methanol and DME in single zone.

It is vital to note that application of absorption process either with dimethyl ether or menthol or their mixture as a scrubbing solvent for recovery of unconverted synthetic gas lean in $CO_2$ from one step DME reactor effluent do not require the investments for purchase of solvent, solvent storage and solvent regeneration facilities because these facilities are inbuilt/exists in the process. Therefore, application of DME and menthol and mixture thereof as solvent seems more attractive option over to the solvents which are not generated in situ in the process like dialkyl ether, potassium carbonate and amine rich solvents. Moreover, the solvents other than DME, methanol and water may also lead the contamination of DME. The contaminated DME can also adversely affect the system where it will be used.

The prior arts documents which disclose the application of DME and menthol and mixture thereof as a solvent to produce pure DME uses number of separation steps to meet the objective for recovery of pure component from product mixture of one step DME reactor. For example; U.S. Pat. No. 6,458,856 B1 teaches the production of pure DME (FIG. 1) involves 7 separating columns and one DME dehydration reactor to separate the syngas, $CO_2$, DME, methanol, and water. In FIG. 2 of this patent (U.S. Pat. No. 6,458,856 B1) water and methanol discharge points from the process are not stated. This implies that water and methanol buildup in the process will increase with the passes of the time and process will become unstable in long run and process scheme is not feasible to implement at actual site of operation. Pat. No. US2010/0216897 disclosing a process shown in FIG. 6 to separate $CO_2$, DME, methanol, and water from DME reactor outlet streams includes 9 separating column.

The person of ordinary skill in the art can understand that $CO_2$ separation from DME, methanol and water mixture using distillation column will require refrigeration or cooling media having temperature much below the room temperature in its condenser for cooling the vapor of this column to the lower temperature to avoid loss of DME product with recovered $CO_2$ stream. This is attributed to high solubility of $CO_2$ in DME, low boiling point value of $-56.6°$ C. for $CO_2$ and requirement of almost complete removal of $CO_2$ from DME, methanol and water mixture to avoid the contamination of DME product with $CO_2$. The quantitative effect of cooling media temperature on DME loss in recovered $CO_2$ stream is illustrated in example 1 of the present invention.

It is essential to note that DME production in two step process wherein methanol is synthesized in one reactor and methanol dehydration is carried out in subsequent second reactor. Methanol synthesis reactor operates at pressure in the range of 70-90 bars and needs huge compression for synthetic gas compression. In one step DME production process, DME synthesis reactor operates in the significantly lower pressure range of 40-60 bars due to enhanced driving force for DME synthesis by simultaneous removal of methanol from system. In two steps DME production process, compression cost is more than 60% of overall process cost.

It is clear that compression cost of synthetic gas in one step process will be much lower than the two step process.

However, process installation and operational cost for recovery of components from product mixture (methanol, unconverted synthetic gas) of methanol synthesis reactor and recovery of components from product mixture (methanol, DME and water) from methanol dehydration reactor is much easier than the recovery of components from single step DME reactor product mixture comprising unconverted synthetic gas, DME, $CO_2$, methanol and water in one step process. The complexity in one step process arises due to requirement of recovered unconverted synthetic gas with significant reduced concentration of $CO_2$, presence of highly volatile DME in product mixture which tend to loss with unconverted synthetic gas, need of refrigeration facilities to generate the cooling medium to be used in the condenser of $CO_2$ separation distillation column for minimizing the loss of DME with recovered $CO_2$ stream.

The methods reported in prior art for separation of DME, $CO_2$, methanol, water, and unconverted synthetic gas from product mixture of one step DME reactor are complicated and capital intensive due to involvement of number of separation steps and expensive refrigeration facilities. Hence, there is a need for a more simpler and cost effective process for separation of DME, $CO_2$, methanol, water, and unconverted synthetic gas from product mixture of one step DME reactor. Therefore, to get the real fruit of less compression requirement and higher per pass conversion of synthetic gas in single DME synthesis reactor and no need of refrigeration facilities in comparison to two step process, a separation process which can simplify the separation scheme to reduce the number of separating steps and can eliminate the need of refrigeration which includes number of equipment in its generation to make the process cost effective and to miniaturize the DME production plant so as it can be used as a modular process will be of great importance.

OBJECTIVE OF THE INVENTION

Main objective of the present invention is to provide a cost effective and energy efficient process for components (DME, $CO_2$, methanol, water, and unconverted synthetic gas) separation from product mixture of one step dimethyl ether synthesis reactor to produce pure dimethyl with purity more than 99.90%.

Another objective of the present invention is to provide a new solvent for recovery of unconverted synthetic gas lean in $CO_2$ and $CO_2$ stream with minimized loss of diethyl ether to enhance the process diethyl ether productivity, recovery of pure dimethyl ether (purity >99.95%) product and recovery of pure methanol (purity >99.95%) to be recycle to DME synthesis reactor.

Yet another objective of the present invention is to provide a process which does not require cooling media having temperature less than room temperature to reduce process installation and operational cost and to miniaturize the process size by eliminating the refrigeration facilities from the process.

Yet another objective of the present invention is to provide an energy and investment efficient method for separating the water and methanol mixture by drastic reduction in flow rate of water and methanol mixture to be processed to meet the process requirement of constant water and methanol concentration in the process even in long run operation.

Still another objective of the present invention is to provide a simple process with reduced number of separating steps for separating the $CO_2$, unconverted synthetic gas, DME, methanol and water from dimethyl ether reactor product mixture for overcoming the disadvantage of prior art processes.

SUMMARY OF THE INVENTION

Accordingly, present invention provides a process for recovery of pure components from product mixture of one step dimethyl ether synthesis reactor comprising the steps of:

a. subjecting the product mixture stream (1) having the pressure in the range of 20 to 50 bars and comprised of DME, $CO_2$, methanol, water, and unconverted synthetic gas to the cooler (2) where it is cooled at temperature in the range of 10 to 70° C. to obtain cooled stream;

b. subjecting the cooled stream (3) as obtained in step (a) to the absorption column (21) where dimethyl ether stream (28) having temperature in the range of 10 to 70° C. is used as $CO_2$ scrubbing solvent to obtain recovered synthetic gas stream;

c. contacting the recovered synthetic gas stream (22) as obtained in step (b) having reduced level of $CO_2$ to the cooler (24) for cooling at temperature in the range of 10 to 70° C. to obtain cooled stream;

d. routing the cooled stream (27) to second absorption column (23) where it is scrubbed with aqueous methanol stream (31) having water to methanol molar ratio in the range of 99 to 0.01 for getting the synthetic gas stream (5) with desired level of $CO_2$ content and for avoiding the dimethyl ether loss with recovered synthetic gas stream (5);

e. routing the stream (6) made of by combining the bottom stream (26) and (25) from absorption columns (21) and (23) to the distillation column (7 for separating the $CO_2$ stream (12) from DME, methanol and water mixture;

f. addition of pure water/aqueous methanol stream (33) to the vapor stream (8) coming from $CO_2$ separation distillation column (7) and subjecting this mixture to water condenser (9) operating with cooling water and separation vessel (11) for recovering the DME free $CO_2$ stream and generating the reflux stream (13) for distillation column;

g. subjecting the $CO_2$ separation distillation column bottom stream (14) to the distillation column 15 for separating the DME from methanol and water mixture;

h. subjecting the methanol and water mixture stream (17A) to distillation column (18) or membrane or adsorption system for separating the methanol and water for their utilization in the process and to be taken out as products for maintaining the component material balance in the process.

In an embodiment of the present invention, product mixture stream (1) is cooled in cooler (2) preferably in the range of 20 to 50° C. and most preferably in the range of 30 to 40° C.

In another embodiment of the present invention, synthetic gas stream (22) is cooled in cooler (24) preferably in the range of 20 to 50° C. and most preferably in the range of 30 to 40° C.

In yet another embodiment of the present invention, dimethyl ether solvent stream (28) temperatures is preferably in the range of 20 to 50° C. and most preferably in the range of 30 to 40° C.

In yet another embodiment of the present invention, aqueous methanol stream (31) has water to methanol molar ratio preferably in the range of 40 to 1, most preferably in the range of 8 to 2.

In yet another embodiment of the present invention, stream (33) is either pure water or aqueous methanol having water to methanol molar ratio preferably in the range of 40 to 1, most preferably in the range of 8 to 2.

In yet another embodiment of the present invention, water mixture stream (17) is divided in two streams (17A) and (32) and the flow rate of (17A) feed to the distillation column 18 is kept in such a way it meets the requirement of withdrawing water and methanol streams from the process without affecting the methanol and water balance in streams used in the process.

In yet another embodiment of the present invention, methanol and water mixture stream (17) is processed either in the membrane or adsorption or distillation system to separate the water and methanol.

In yet another embodiment of the present invention, purity of DME, methanol and water stream is in the range of 80 to 100 mole % preferably in the range of 95 to 100 mol % and most preferably in the range of 99.9 to 100 mol %.

DETAILED DESCRIPTION OF THE PREFERRED EMBODIMENT

Present invention relates a process for recovery of pure components dimethyl ether (DME), $CO_2$, methanol, water, and unconverted synthetic gas) from product mixture of one step dimethyl ether synthesis reactor to overcome the disadvantages of prior art processes and comprises of following steps:

a. subjecting the cooled product mixture of one step dimethyl ether synthesis reactor to the absorption column where dimethyl ether is used as solvent for $CO_2$ scrubbing;

b. subjecting the effluent of first absorption column to water cooler and contacting the cooled effluent with aqueous methanol in second absorption column for getting the unconverted synthetic gas with desired $CO_2$ content and to capture the dimethyl ether form recovered unconverted synthetic gas;

c. combining the bottom streams from absorption columns and routing of combined stream to the distillation column for separation of $CO_2$;

d. addition of water/aqueous methanol to the vapor of $CO_2$ separation distillation column and subjecting this mixture to water cooler followed by separation vessel for recovering the DME free $CO_2$ stream and generating the reflux stream for distillation column;

e. subjecting the $CO_2$ separation distillation column bottom stream to another distillation column for separating the dimethyl ether from methanol and water;

f. subjecting the full or partly methanol and water mixture stream to another distillation column/membrane for separating the methanol and water either for their utilization in the process or to be taken out as withdrawn products.

The present invention relates to a cost effective, energy efficient, environment friendly and miniaturized process for recovery of pure components from product mixture of one step dimethyl ether synthesis reactor, wherein the process of present invention comprising of the following steps:

a. subjecting the product mixture stream (1) having the pressure in the range of 20 to 50 bars and comprised of DME, $CO_2$, methanol, water, and unconverted synthetic gas to the cooler (2) where it is cooled in the range of 10 to 70° C.;

b. subjecting the cooled stream (3) to the absorption column (21) where dimethyl ether stream (28) having temperature in the range of 10 to 70° C. is used as $CO_2$ scrubbing solvent;

c. contacting the recovered synthetic gas stream (22) having reduced level of $CO_2$ to the cooler (24) for cooling it in the range of 10 to 70° C.;

d. routing the cooled stream (27) to second absorption column (23) where it is scrubbed with aqueous methanol stream (31) having water to methanol molar ratio in the range of 99 to 0.01 for getting the synthetic gas stream (5) with desired level of $CO_2$ content and for avoiding the dimethyl ether loss with recovered synthetic gas stream (5);

e. routing the stream (6) made of by combining the bottom stream (26) and (25) from absorption columns (21) and (23) to the distillation column (7) for separating the $CO_2$ stream (12) from DME, methanol and water mixture;

f. addition of pure water/aqueous methanol stream (33) to the vapor stream (8) coming from $CO_2$ separation distillation column (7) and subjecting this mixture to water condenser (9) operating with cooling water and separation vessel (11) for recovering the DME free $CO_2$ stream and generating the reflux stream (13) for distillation column;

g. subjecting the $CO_2$ separation distillation column bottom stream (14) to the distillation column (15) for separating the DME from methanol and water mixture;

h. Splitting the stream (17) is divided in two streams (17A) and (32). The flow rate of (17A) feed to the distillation column is kept in such a way it meets the requirement of withdrawing water and methanol streams from the process without affecting the methanol and water balance in streams used in the process;

i. Subjecting the stream 17 to either distillation column 18 or membrane (not shown in figure) or adsorption system (not shown in figure) for separating the water and methanol;

j. Taking out the required amount of pure methanol as stream 30 or purging the water as stream 34 to maintain the balance of methanol and water in the process.

Recovered unconverted synthetic gas lean in $CO_2$ can be either recycled to dimethyl ether reactor or can be purged to flare or can be used as a fuel in reformer to produce synthetic gas.

Withdrawn streams of methanol can be used either separate methanol dehydration reactor to produce DME or can be recycled to the one step dimethyl ether synthesis reactor.

For the purpose of illustrating the invention, drawings constructed in accordance of prior art and preferred embodiments of the present invention are conceptualized. The same numeral is used in drawings to refer the same or similar element or stream or column. It is important to note that invention is not limited to the precise arrangements of apparatus shown in drawings. Present invention relates a process for recovery of pure components (dimethyl ether (DME), $CO_2$, methanol, water, and unconverted synthetic gas) from product mixture of one step dimethyl ether synthesis reactor. To describe the present invention in detail, reference is made to the FIGS. 1, 2, 3, and 4.

Figure 1:
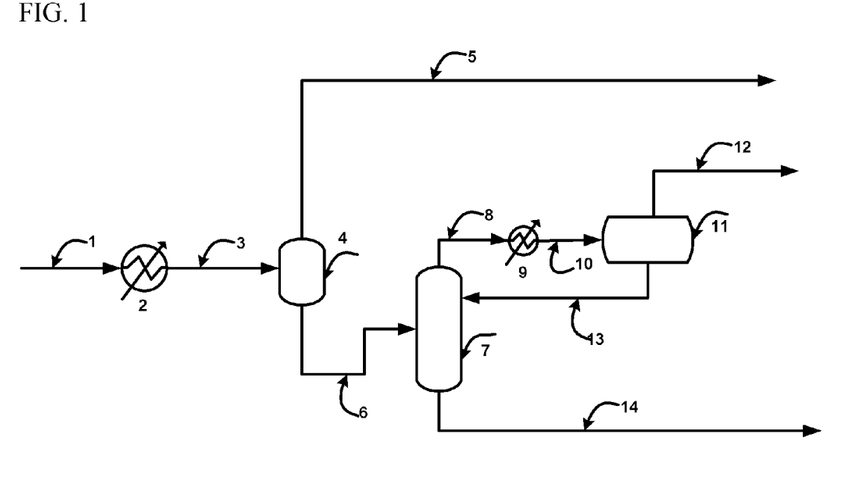
FIG. 1 is a systematic representation of process based on cryogenic separation of $CO_2$ from product mixture of one step dimethyl ether synthesis reactor to demonstrate the need of refrigeration and effect of process parameter on the process performance. It involves the chilling of one step dimethyl ether synthesis product mixture followed by flash stage and distillation column for recovery $CO_2$ lean synthetic gas and $CO_2$ stream respectively.

Referring to FIG. 1 wherein product mixture comprising DME, $CO_2$, methanol, water, and unconverted synthetic gas stream (1) having the pressure in the range of 20 to 50 bars and temperature in the range of 200 to 270° C. is cooled in the cooler (2) to reduce its temperature in the range of −40.0 to 10.0° C. The cooled stream (3) is fed to the single stage flash (4) to separate the unconverted synthetic gas from its associated compounds. Unconverted synthetic gas lean in $CO_2$, DME, and methanol and water stream (5) is routed to the compressor for its recycle to the DME reactor (not shown in the FIG. 1). Stream (6) comprising $CO_2$, DME, methanol and water is fed to the distillation (7). The vapor stream (8) from column (7) is cooled in the cooler (9) in the temperature range −2.0 to 13.0° C. depending up on the allowable DME loss with the recovered $CO_2$ stream (12). The cooled stream (10) is subjected to the separating vessel (11) for recovering the $CO_2$ as stream (12) and generating the reflux to column stream (13). The column (7) bottom stream (14) comprising DME, methanol and water can be routed to subsequent separating units to obtain the pure DME, methanol and water either using distillation or some other method.

Figure 2:
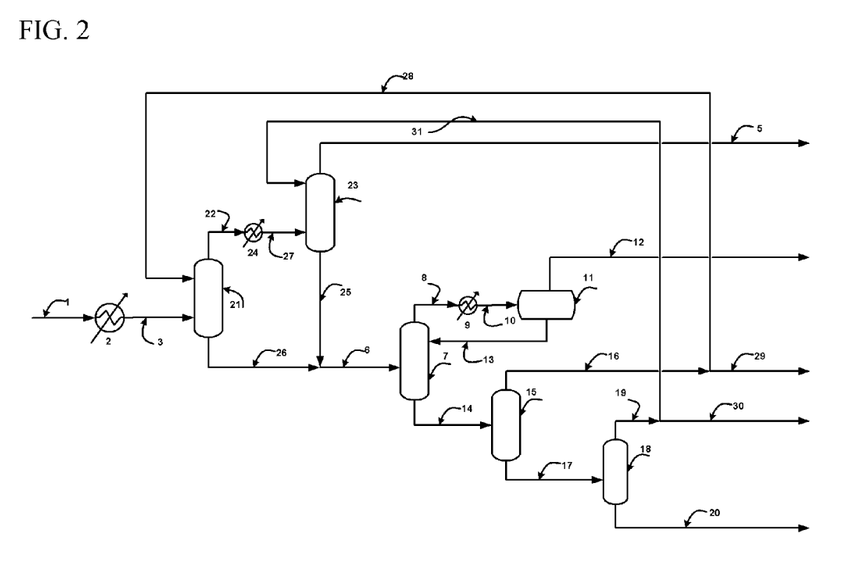
FIG. 2 is a systematic representation of the process conceptualized to construct a comparative example for establishing the basis for demonstrating the benefits of present invention over closest process using of pure methanol or DME or their mixture for $CO_2$ removal and components (DME, $CO_2$, methanol, water, and unconverted synthetic gas) separation from product mixture of one step dimethyl ether synthesis reactor to produce pure dimethyl with purity more than 99.90%.

Referring to FIG. 2 which is representing the process involving absorption steps with either pure methanol and pure DME or their mixture as solvents already disclosed in the prior art. The process scheme is conceptualized to demonstrate the benefits of present invention for using the pure DME and aqueous methanol as solvent against using pure methanol and pure DME or their mixture as solvents for minimizing the loss of DME and methanol with recovered unconverted synthetic gas to enhance process dimethyl ether productivity, to reduce the energy requirement, to reduce the installation and operation cost of methanol and water separation distillation column and to improve the overall performance of the process.

In this process, stream (1) is cooled in cooler (2) in the temperature range of 25 to 50° C. depending on the pressure of DME reactor (Not shown in Figure). Cooled stream (3) is fed to the absorption column (21) where it is contacted with pure dimethyl ether (DME) stream (28) in a counter current fashion. Stream (22) with reduced level of $CO_2$ and DME is cooled in the cooler (24) in the temperature range of 25 to 50° C. The cooled stream (27) is fed to absorption column (23) where it is contacted with either pure methanol to remove the DME and $CO_2$ from the recovered synthetic gas as stream (24). Stream (24) can be recycled to the DME reactor (not shown in FIG. 2). The stream (27) consists of stream (26) coming from column (21) and stream (25) coming from column (23) is fed to the distillation column (7) for recovery of $CO_2$ and other gases dissolved in DME and Methanol in column (21) and column (23). The vapor stream (8) from column (7) is cooled in cooler (9) in the temperature range of −2 to 13.0° C. The cooled stream (10) is sent to the separating vessel (11) for recovering of dissolved gases as $CO_2$ stream (12) and generating the reflux stream (13) to the column (7). The column (7) bottom stream (14) is routed to distillation column (15) for separating the DME as stream (16) and methanol and water mixture as stream (17). Stream (16) is divided in stream (29) to withdrawn the DME product and stream (28) to be used as solvent in the process. Stream (17) is fed to the distillation column (18) for separating the methanol as stream (19) and water as stream (20). Stream (19) is further divided in stream (31) to be used as solvent in process and stream (30) to be withdrawn methanol as product.

Figure 3:
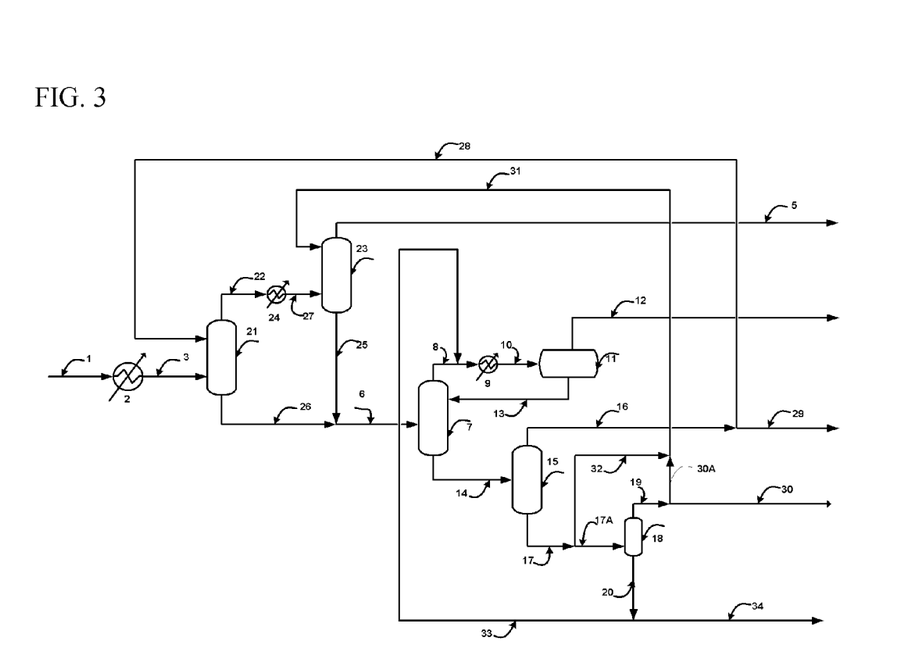
FIG. 3 is a systematic representation of process constructed in accordance of one of the embodiments of the present invention for using the pure DME and aqueous methanol as solvent for $CO_2$ removal from unconverted syngas obtained from one step DME reactor, new processing scheme of $CO_2$ separation distillation column to remove the need of cooling media having temperature less than zero degrees centigrade in condenser of $CO_2$ separation distillation column by cooling water for reducing the energy, elimination of refrigeration system requirement and reducing the installation and operational cost of process.

Referring to FIG. 3, representing the process, constructed in accordance of the present invention to one of the embodiment of the present invention for demonstrating new processing scheme of $CO_2$ separation distillation column to remove the need of cooling media having temperature less than zero degrees centigrade in condenser for elimination the need of refrigeration facilities in the process thereby reducing the energy, installation and operation cost of process. This process has same configuration and operation as shown in FIG. 2 till the stream (6) is fed to the distillation column (7). Further, vapor stream (8) is mixed with the water stream (33) before entering to the cooler (9) where mixed stream is cooled in the temperature range of 30 to 50° C. depending on the allowable limit of DME with recovered $CO_2$ and associated gases. The cooled stream (10) is fed to the vessel (11) for separation of $CO_2$ gas stream (12) and liquid reflux stream (13) to column (7). The column (7) bottom stream (14) is fed to the column (15) for producing the pure DME stream (16) and aqueous methanol stream (17). The DME stream (16) is divided into stream (28) to be used as solvent in the column (21) and stream (29) as product withdrawn from the process. The stream (17) is also divided in stream (17A) to be used as feed to distillation column (18) and stream (32). The methanol stream (19) from column (18) is divided in stream (30) to be taken out methanol product withdraw and stream (30A) to be mixed with stream (32) to maintain the given methanol concentration in stream (31). The column (18) bottom water streams (20) is divided in stream (34) for water withdrawn from process and stream (33) for mixing with stream (8).

Referring to FIG. 5, representing the process constructed accordance to one of the embodiment of the present invention for demonstrating quantitative benefits of new processing scheme of aqueous methanol mixture separation into water and methanol for further reducing the energy installation and operational cost of either water and methanol distillation column or membrane in comparison to the process described in FIG. 3. This process has same configuration and operation as shown in FIG. 3 till the processing of stream (17) except that stream (33) is comprises of aqueous methanol in place of pure water. The aqueous methanol stream (17) is divided in streams (17A) to be used as feed either to distillation column/membrane unit (18) and stream (32). Water stream (20) from unit (18) is splitted into stream (34) to be taken as water withdraw from process and stream (34A) to be mixed with aqueous methanol stream (32) to maintain the given concentration of methanol in stream (35) which is divided in stream (31) to be used as solvent in absorption column (23) and stream (33) for mixing with stream (8).

It is important to note that closest prior art for production of pure dimethyl ether through one step process teaches the application of pure dimethyl ether and pure methanol to scrub the $CO_2$ from the product mixture of dimethyl ether synthesis reactor to reduce the $CO_2$ level in recovered synthetic gas and application of mixture of dimethyl ether and methanol to minimize loss of dimethyl ether and methanol in unconverted synthetic gas for enhancing the dimethyl ether productivity of the process and application of pure DME and Pure methanol in separate zone of distillation column to reduce the quantity of solvent required in the process. These processes involve a large number of separation steps for recovery of DME, $CO_2$, methanol, water, and unconverted synthetic gas from product mixture of one step DME reactor. It is apparent to the one of skill in the art that large number of separation steps increase the size, installation cost, operational cost, and foot print of the process. These processes used huge amount of methanol as solvent. Product mixture from dimethyl ether synthesis reactor contains small amount of water. Product mixture is scrubbed using DME and methanol which dissolve the small quantity of water along with $CO_2$. Therefore, the small amount of water from huge quantity of methanol needs to be removed from the process to maintain the purity of methanol to be used as a solvent. The boiling point of methanol and water are 64.4° C. and 100° C., respectively. Therefore, separation of this small amount of water from methanol will results in vaporization of huge quantity of methanol which needs enormous energy and large diameter of distillation column to be used in this separation.

Further, to produce the pure dimethyl ether (DME) from mixture of DME, $CO_2$, methanol, water, $CO_2$ recovery using the distillation column even operated at high pressure needs cooling media having temperature much lower than the room temperature in the condenser to cool the vapor stream to a low temperature for reducing the loss of DME in recovered $CO_2$ stream. Lower temperature requirement of vapor stream is attributed to boiling point of $CO_2$ (−56.6° C.) and DME (−34.0° C.), significant $CO_2$ solubility in DME, requirement of deep removal of $CO_2$ from mixture to avoid the contamination of DME, and minimizing the loss of DME with recovered $CO_2$ to enhance the DME productivity of process. Accordingly, refrigeration facilities are required in the process to generate the cooling media to be used in the condenser of $CO_2$ separation column to cool the vapor of $CO_2$ to the desired temperature. Refrigeration facilities requirement not only add the investment cost the process but also increase the operational cost and operational complexity of the process.

Novelty of the present invention relies in use of aqueous methanol as a new kind of solvent for minimizing the loss of DME and methanol with recovered unconverted synthetic gas which results in improved process dimethyl ether productivity. Application of aqueous methanol also facilitates the significant reduction in vaporization of methanol in the process to maintain the methanol and water balance in the process required by drastic reduction in the quantity of methanol and water mixture to be separated. The aqueous methanol to be processed in distillation column 18 has much more water than the water present in the product mixture of dimethyl synthesis reactor. For maintaining the water balance in the process, water quantity equivalent to water present in product mixture is to be removed from the aqueous methanol stream (17). Thus, present process gives the opportunity to process the minor portion of stream (17) in distillation column to withdrawn the required amount of water from the process. Thus, invention leads to drastic reduction in energy requirement, cost of installation and operation of methanol and water separation distillation column and thus improves the overall performance of the process significantly.

Further novelty of present invention bank on the innovative new configuration and operational scheme used for $CO_2$ separation column for eliminating the requisite refrigeration facility to generate the cooling medium having the temperature much less than room temperature or subzero temperature required in the condenser of $CO_2$ separation column to cool the vapor stream to desired temperature to restrict the loss of DME with recovered $CO_2$ stream. Thereby, invention not only reduces the installation and operational cost of the process drastically, but also miniaturizes and simplifies the process operation. It is important to note that in the present invention the volume of aqueous methanol to be processed for recovery of water and methanol is small and facilitating the use of economic membrane method in place of methanol water distillation column and provides the further opportunity for plant miniaturization and energy savings.

In the process of present invention all the components present in the product mixture of DME reactor have taken out as withdrawal product streams to maintain these components concentration consistent in the process for a stable long run operation which is missing part in most of the prior art processes. No prior art teaches this kind of energy efficient, cost effective and simple process provided in present invention which can be easily implemented at the actual site of operation and has huge commercial potential.

EXAMPLES

Following examples are given by way of illustration to substantiate the invention and therefore should not be construed to limit the scope of the invention.

Data of examples is generated using a process simulation computer program in connection with the process diagramed in FIGS. 1 to 4. The process simulation program was first validated with the literature data for the separation of the compounds present in the product mixture of one step dimethyl ether synthesis reactor. The molar flow rate of 100 kmole/h and composition of product mixture comprises of $CO_2$, DME, $H_2$, CO, methanol and water with mole % of 41.3, 41.5, 6.0, 8.0, 2.0, and 1.5, respectively is used as a starting feed in all the following examples for demonstrating the invention. The operating pressure of cooler, absorption column, distillation columns used for separating the components of product mixture are also kept constant for each example to maintain the consistency of data for a realistic comparison. Moreover, DME and methanol purity greater than 99.6 mol %, and water purity greater than 99.8 mol % is maintained in examples 2 to 5.

Comparative Example 1

This example is in reference to FIG. 1. It illustrates the effect of cooling temperature of stream 3 (pressure=39.5 bars) comprises of $CO_2$, DME, $H_2$, CO, methanol and water in the mole % of 41.3, 41.5, 6.0, 8.0, 2.0, 1.5, respectively which is cooled in the cooler (2) and fed to single stage flash on DME carry over in recovered synthetic gas stream (5); effect of pressure of stream (3), which depends on DME reactor pressure and controls the cooler operating pressure, on required cooling temperature stream (3) for maintaining the 10000 ppm DME loss in synthetic gas; and effect of cooling temperature of stream (8) or condenser (9) (pressure of 39 bars) produced from $CO_2$ separation distillation column (7) on DME loss in $CO_2$ stream (12). The feed stream (6) to the column (7) have composition of 45.6, 2.3, 0.5, 1.4, 2.4 and 47.7 mol % for $CO_2$, CO, $H_2$, water, methanol and DME respectively. Sensitivity analysis of these parameters on DME loss/carryover is carried out and results are given in Table 1.

TABLE 1

| Effect of temperature on DME carryover/loss in syngas | | Effect of Pressure on required cooling temperature of stream 3 | | Effect of temperature on DME carryover in $CO_2$ stream 12 | |
|---|---|---|---|---|---|
| Temp. of stream 3, ° C. | DME content, PPM | Pressure of steam3, bar | Cooling Temperature, ° C. | Temp. of stream8, ° C. | DME carryover, PPM |
| −40 | 10000 | 30 | −45 | 0.7 | 638 |
| −30 | 17000 | 35 | −42 | 4.1 | 13000 |
| −20 | 26000 | 40 | −40 | 7.2 | 24000 |
| −10 | 40000 | 45 | −39 | 10.1 | 36000 |
| 0 | 58000 | 50 | −36 | 12.7 | 47000 |

Results in table 2 indicate that there is a need of refrigerant/cooling medium having temperature much below the room temperature to restrict the DME loss in synthetic gas stream (5) and in $CO_2$ stream (12). Thus, this process needs to include refrigeration facilities. Though, results in Table 1 indicates that temperature of cooling media to be used in the cooler (3) for cooling the stream (3) to desired level increases with increase in pressure and thereby will reduce the marginal load of refrigeration facility, but it will force to run the DME at higher pressure. High pressure of DME reactor will increase the cost of compression for synthetic gas.

Comparative Example 2

This example is in reference to FIG. 2. The feed stream (1) having pressure of 40.5 bars is cooled in cooler (2) operated at pressure 40.0 bars to the temperature of 36° C. The cooled stream (3) is subjected to absorption column (21) operate at top pressure of 39.5 bars for scrubbing the $CO_2$ using the DME as a solvent. The gaseous effluent stream (22) is cooled in cooler (24) operated at pressure of 39 bars to the temperature of 36° C. and fed to the second absorption column (23) operated at top pressure of 38.5 bars using the pure methanol solvent as solvent having flow rate 58 kmol/h to capture the DME and $CO_2$ from cooled effluent stream (27). The stream (6) made of streams (26) and (25) is processed in distillation column (7) comprising of 20 trays with the top pressure of 38.5 bars. The stream (8) is cooled to 0.8° C. in cooler (9) before feeding to separating vessel (11) operated at 38.0 bars. The $CO_2$ from the stream (6) is removed as stream (12). The stream (14) comprising DME, methanol and water is processed in distillation column (15) with condenser pressure of 9.5 bar to obtain the pure DME product as stream (29) and DME stream (28) to be used as solvent by maintaining the required reflux rate. The methanol and water mixed stream (17) is fed to the distillation column (18) operated with condenser pressure of 1.2 bar for separating the water and methanol as streams (20) and (19) respectively.

The performance and economic parameters for this example are given in Table 2.

TABLE 2

Performance parameters

| | |
|---|---:|
| $CO_2$ content in recovered synthetic gas 5, mol % | 1.04 |
| DME+ methanol content in recovered synthetic gas 5, ppm | 7373 |

Economic parameters

| | *DC-7 | *DC-15 | *DC-18 |
|---|---:|---:|---:|
| Condenser temperature, ° C. | 0.80 | 42.4 | 68.9 |
| Condenser Duty, cal/sec | 61566.4 | 344217.7 | 417637.0 |
| Reboiler temperature, ° C. | 125.8 | 137.2 | 114.5 |
| Reboiler Duty, cal/sec | 268511.1 | 215657.8 | 381305.5 |
| Maximum vapor flow in column, scmh | 8372.7 | 6694.8 | 4039.7 |

*DC-7, *DC-15 and *DC-18 are $CO_2$ separation, DME separation and methanol and water separation distillation Column respectively.

From the results it can be observe that scrubbing of product mixture obtained from the dimethyl ether synthesis reactor in absorber column (21) using the DME as solvent and in subsequent absorber column (23) using the methanol as solvent reduces the concentration of $CO_2$ in unconverted syngas from 74.7% to 1.04%. There is need of cooling media having the temperature at least less than −4.0 C (considering around 5° C. temperature difference between cooling medium stream and process stream for heat transfer) to cool the vapor stream 8 of column (7) up to 0.8° C. for separation of $CO_2$ stream from stream (6). However, still there is a loss of DME and methanol to the amount of 7373 ppm with unconverted synthetic gas.

Example 3

This example is in reference to FIG. 3. Aqueous methanol comprising methanol and water in molar ratio of 4 having 65.3 kmol/h flow rate is used as solvent in absorber column (23) in place of pure methanol used in example 2. The column vapor stream (8) is mixed with the stream (33) comprising of pure water. The mixed stream (8A) is fed to the cooler (9) where it is cooled to 36° C. before entering to the separating vessel (11). The stream (20) is divided in stream (34) to withdrawn water from process and stream (33) to be used for mixing with stream (8). Stream (19) is divided in stream (30) to withdrawn methanol from process and stream (30A) to be mixed with stream (32) to maintain water concentration in stream (31) to be used as solvent. For the same products quality and quantity as obtained in example 3, performance parameters for this example are given in Table 3.

TABLE 3

Performance parameters

| | |
|---|---:|
| $CO_2$ content in recovered synthetic gas 5, mol % | 0.96 |
| DME+ methanol content in recovered synthetic gas 5, ppm | 2766 |

Economic parameters

| | *DC-7 | *DC-15 | *DC-18 |
|---|---:|---:|---:|
| Condenser temperature, ° C. | 36.0 | 42.3 | 69.0 |
| Condenser Duty, cal/sec | 63844.2 | 344417.1 | 53602.0 |
| Reboiler temperature, ° C. | 144.0 | 162.8 | 115.1 |
| Reboiler Duty, cal/sec | 323200.0 | 192107.0 | 39242.0 |
| Maximum vapor flow in column, scmh | 7532.7 | 6695.0 | 1212.9 |

*DC-7, *DC-15 and *DC-18 are $CO_2$ separation, DME separation and methanol and water separation distillation Column From the results it can be seen that using the aqueous methanol in second absorption (23) leads to greater reduction in $CO_2$ with significantly reduced DME and methanol loss with unconverted syngas and DME loss in recovered $CO_2$ stream (12). A comparison analysis of results given in Table 2 and Table 3 reveals that application of aqueous solvent reduces DME plus methanol loss in recovered synthetic gas by 62.5%. Moreover it can be seen that the condenser temperature of $CO_2$ separation (7) is 36° C. in comparison to the temperature of 0.8° C. maintained in example 2 to 4 where simple distillation column without mixing the external water stream with the vapor stream of column is used. For the one of skill in the art, it is apparent the condenser temperature of 36° C. can be attained using the cooling water having room temperature around 25° C. and thereby invention eliminate the need of refrigeration facility to produce the cooling media having temperature at least less than −3° C. to attain the condenser temperature of 0.8° C. Moreover, it shall be noted that combined re-boiling duty and condensing duty is present invention is lower by 35.9 and 43.9% respectively in comparison to example 2.

Example 4

Figure 4:
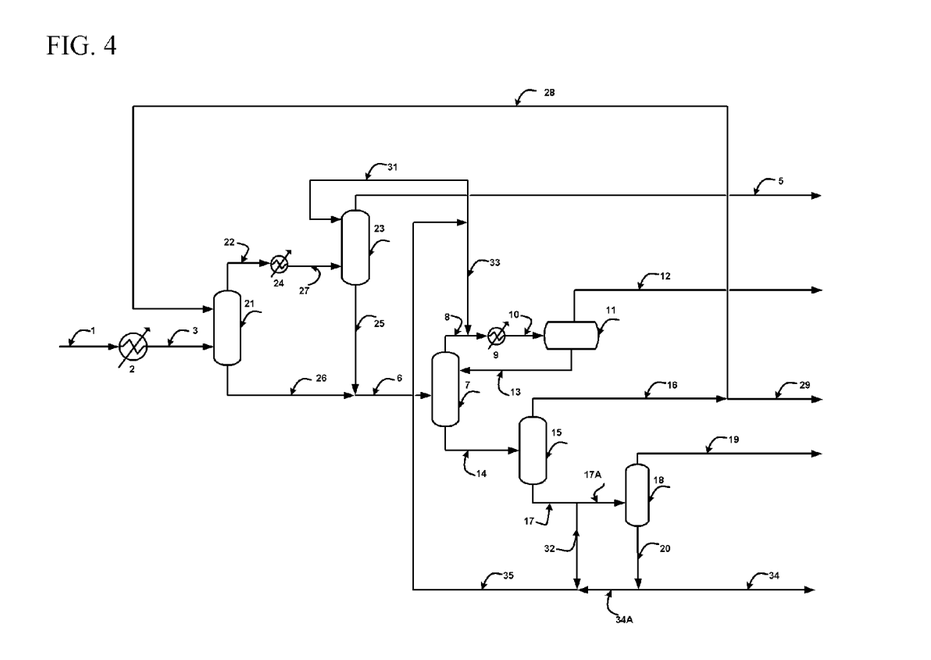
FIG. 4 is a systematic representation of another variation of process, constructed in accordance of one of the embodiment of the present invention, described in FIG. 3 for demonstrating new processing scheme of aqueous methanol mixture separation into pure water and methanol for further reducing the energy, installation and operational cost of either water and methanol distillation column or membrane.

This example is in reference to FIG. 4. The aqueous methanol having methanol and water ratio of (4) against the pure water as used in example 4 was used as mixing stream (33) with the vapor stream 8 before entry to condenser (9). The processing of aqueous methanol stream (17) processing in distillation column (18) was also modified using innovative approach. The stream (17) is divided in stream (17A) and (32) in such a ratio that stream (17) contains only enough methanol quantity which to be withdrawn from the process. The column (18) output stream (20) is divided in stream (34) to withdrawn the water from the process and stream (34A) for mixing with stream (32) to maintain the methanol concentration in stream (31) to be used as solvent and stream (33) to be used as mixing stream. The performance and economic parameters for this example are given in Table 4.

TABLE 4

Performance parameters

| | |
|---|---:|
| $CO_2$ content in recovered synthetic gas 5, mol % | 0.96 |
| DME+ methanol content in recovered synthetic gas 5, ppm | 2766 |

Economic parameters

| | *DC-7 | *DC-15 | *DC-18 |
|---|---:|---:|---:|
| Condenser temperature, ° C. | 36 | 41.9 | 69.0 |
| Condenser Duty, cal/sec | 20365.1 | 346102.0 | 16785.0 |
| Reboiler temperature, ° C. | 137.16 | 158.8 | 115.0 |
| Reboiler Duty, cal/sec | 263281.9 | 195067.0 | 13031.0 |
| Maximum vapor flow in column, scmh | 7653.12 | 6702.2 | 161.7 |

*DC-7, *DC-15 and *DC-18 are $CO_2$ separation, DME separation and methanol-water separation distillation Column.

This example illustrates the effect of application of aqueous methanol to eliminate the requirement of cooling medium of having temperature much below the room temperature in condenser of $CO_2$ separation column 7 on condenser duty, reboiler duty and maximum vapor flow of water and methanol separation column. It is of immense interest to note that for the process shown in this example, condenser duty, reboiler duty and maximum vapor flow of water and methanol separation column (18) are lower by 68% in comparison to example 4. There is no need of refrigeration facility in the process. Moreover, it shall be noted that combined re-boiling duty and condensing duty is present invention is lower by 45.5 and 53.5%, respectively in comparison to example 2. However, there is loss of 2000 ppm of methanol with $CO_2$ stream 12.

Present invention facilitates us to get the real fruits of low operating pressure and high conversion of synthetic gas in one step dimethyl ether synthesis reactor by resolving the challenge of complicated separation system requirement for separating the components of product mixture obtained from single dimethyl ether synthesis reactor by providing the simple, economical, miniaturized, energy efficient and refrigeration free process.

ADVANTAGES OF THE INVENTION

The major benefits of process for recovery of pure components from product mixture of one step dimethyl ether synthesis reactor of the present invention over the closest prior arts are as follows:

- Lower loss of methanol and DME in the recovered $CO_2$ lean synthetic gas to be recycled to DME reactor and thus enhanced process DME productivity.
- No refrigeration facilities/refrigeration utility/cooling media having the temperature less than zero degrees centigrade is required to restrict the DME loss in recovered $CO_2$ stream. Thus, reducing the size and cost of the process drastically and leads to the miniaturization of DME process.
- Momentous reduction in size and energy requirement for methanol and water separation in the process which results in further significant reduction in energy, cost and size of methanol and water separation unit (distillation column or membrane).
- Significantly, reduced volume of methanol and water mixture separation facilitates application of small membrane system to separate methanol and water and thus further creates the scope of miniaturization of DME process.
- Miniaturization of process creates the scope for making the modular dimethyl ether production process.
- Environment friendly process.

What is claimed is:

1. A process for recovery of pure components from a product mixture of one step dimethyl ether synthesis reactor comprising:
    a) subjecting a product mixture stream having a pressure in a range of 20 to 50 bars and comprised of dimethyl ether (DME), $CO_2$, methanol, water, and an unconverted synthetic gas to a cooler where the product mixture stream is cooled at a temperature in a range of 10 to 70° C. to obtain a cooled stream;
    b) subjecting the cooled stream obtained in the step (a) to an first absorption column where dimethyl ether stream having a temperature in a range of 10 to 70° C. is used as a $CO_2$ scrubbing solvent to obtain a top stream comprising a recovered synthetic gas stream and a bottom stream;
    c) contacting the recovered synthetic gas stream obtained in the step (b) having a reduced level of $CO_2$ to the cooler for cooling at a temperature in a range of 10 to 70° C. to obtain a cooled stream;
    d) routing the cooled stream obtained in the step (c) to a second absorption column where the cooled stream obtained in the step (c) is scrubbed with aqueous methanol stream having water to methanol molar ratio in a range of 99 to 0.01 mol % to obtain a top stream comprising synthetic gas stream with a desired level of $CO_2$ content and a bottom stream to avoid a dimethyl ether loss with the synthetic gas stream;
    e) routing a stream made by combining bottom streams from the first and second absorption columns to a $CO_2$ separation distillation column to separate a $CO_2$ stream from DME, methanol and water mixture;
    f) adding a pure water, aqueous methanol or pure methanol stream to a vapor stream coming from the $CO_2$ separation distillation column, and subjecting a mixture of the pure water/aqueous methanol stream and the vapor stream to a water condenser operating with cooling water and a separation vessel for recovering DME free $CO_2$ stream, and generating a reflux stream for distillation column;
    g) subjecting a $CO_2$ separation distillation column bottom stream to the distillation column for separating DME from methanol and water mixture;
    h) subjecting the methanol and water mixture stream to a distillation column or a membrane or an adsorption system for separating methanol and water for their utilization in a process and to be taken out as products for maintaining a component material balance in the process.

2. The process according to claim 1, wherein the product mixture stream is cooled in the cooler in a range of 20 to 50° C.

3. The process according to claim 1, wherein the synthetic gas stream obtained in the step (b) is cooled in the cooler in a range of 20 to 50° C.

4. The process according to claim 1, wherein the temperature of the dimethyl ether stream in step (b) is in a range of 20 to 50° C.

5. The process according to claim 1, wherein the aqueous methanol stream has water to methanol molar ratio in a range of 40 to 1 mole %.

6. The process according to claim 1, wherein the stream of step (f) is aqueous methanol having water to methanol molar ratio in a range of 40 to 1 mole %.

7. The process according to claim 1, wherein the methanol and water mixture stream processed in the distillation column is divided in two streams and a flow rate of the methanol and water mixture stream fed to the distillation column is kept to meet a requirement of withdrawing water and methanol streams from the process without affecting the methanol and water balance in the streams used in the process.

8. The process according to claim 1, wherein a purity of DME, methanol and water stream is in a range of 80 to 100 mole %.

9. The process according to claim 1, wherein the product mixture stream is cooled in the cooler in a range of 30 to 40° C.

10. The process according to claim 1, wherein the synthetic gas stream of step (b) is cooled in the cooler in a range of 30 to 40° C.

11. The process according to claim 1, wherein the temperature of the dimethyl ether stream of step (b) is in a range of 30 to 40° C.

12. The process according to claim 1, wherein the aqueous methanol stream has water to methanol molar ratio in a range of 8 to 2 mole %.

13. The process according to claim 1, wherein the stream of step (f) is aqueous methanol having water to methanol molar ratio in a range of 8 to 2 mole %.

14. The process according to claim 1, wherein a purity of DME, methanol and water stream is in a range of 95 to 100 mol %.

15. The process according to claim 1, wherein a purity of DME, methanol and water stream is in a range of 99.9 to 100 mol %.

* * * * *